United States Patent [19]

DiNinno

[11] 4,123,539
[45] Oct. 31, 1978

[54] 6-ETHYLPENICILLANIC ACID

[75] Inventor: Frank P. DiNinno, Old Bridge, N.J.

[73] Assignee: Merck & Co., Inc., Rahway, N.J.

[21] Appl. No.: 865,639

[22] Filed: Dec. 29, 1977

[51] Int. Cl.$^2$ .................. A61K 31/425; C07D 513/04
[52] U.S. Cl. .............................. 424/270; 260/306.7 C
[58] Field of Search .................. 260/306.7 C; 424/270

[56] References Cited

U.S. PATENT DOCUMENTS

| | | | |
|---|---|---|---|
| 3,206,469 | 9/1965 | Pifferi .............................. | 260/306.7 C |
| 3,821,198 | 6/1974 | Lee et al. ...................... | 260/306.7 C |
| 3,936,446 | 2/1976 | Bentley et al. ................ | 260/306.7 C |
| 3,974,150 | 8/1976 | Cook et al. .................... | 260/306.7 C |

*Primary Examiner*—Jose Tovar
*Attorney, Agent, or Firm*—Frank M. Mahon; James A. Arno; Julian S. Levitt

[57] ABSTRACT

Disclosed are the antibiotics 6-ethylpenicillanic acid and 6-ethylpenicillanic acid sulfoxide (I):

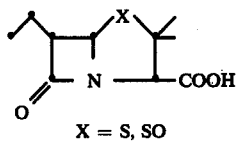

X = S, SO

Also disclosed are processes for preparing I and its pharmaceutically acceptable salts and esters; pharmaceutical compositions comprising such compounds; and methods of treatment comprising administering such compounds and compositions when an antibiotic effect is indicated.

3 Claims, No Drawings

6-ETHYLPENICILLANIC ACID

BACKGROUND OF THE INVENTION

This invention relates to 6-ethylpenicillanic acid and 6-ethylpenicillanic acid sulfoxide (I) and their pharmaceutically acceptable salts and esters which are useful as antibiotics:

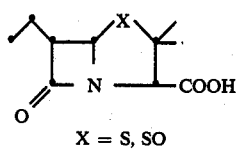

X = S, SO

This invention also relates to processes for preparing I; pharmaceutical compositions comprising I and methods of treatment comprising administering I when an antibiotic effect is indicated.

There is a continuing need for new antibiotics. For unfortunately there is no static effectiveness of any given antibiotic because continued wide scale usage selectively gives rise to resistant strains of pathogens. In addition, the known antibiotics suffer from the disadvantage of being effective only against certain types of microorganisms. Accordingly the search for new antibiotics continues.

Thus, it is an object of the present invention to provide a novel antibiotic and the pharmaceutically acceptable salts and esters thereof which are useful in animal and human therapy and in inanimate systems. These antibiotics are active against a broad range of pathogens which representatively include both gram positive bacteria such as *S. aureus, Strep. pyogenes* and *B. subtilis,* and gram negative bacteria such as *E. coli, Proteus morganii, Serratia* and *Klebsiella.* Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I) are prepared according to the following scheme:

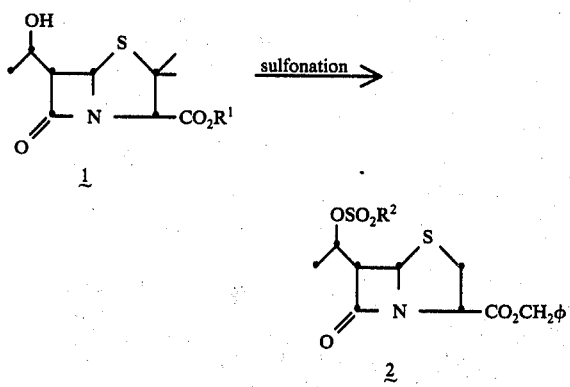

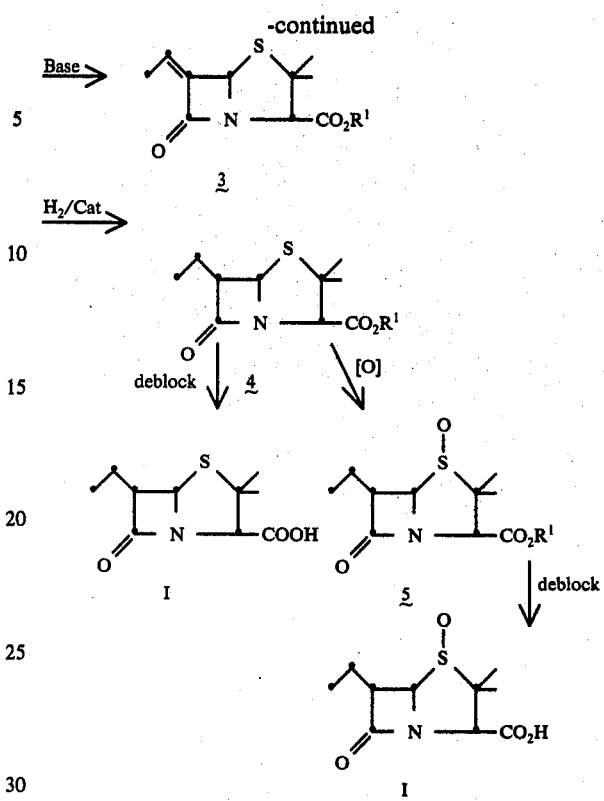

wherein: $R^1$ is a readily removable blocking group such as benzyl, p-nitrobenzyl, trichloroethyl, methyl or the like; or $R^1$ is a pharmaceutically acceptable ester moiety such as pivaloyloxymethyl, 3-buten-1-yl, (2-methylthio)-ethyl, or the like; and wherein $R^2$ is $O^-M^+$, M is hydrogen or any non-critical cation such as an alkali metal or organic base; or $R^2$ is alkyl or an aryl radical such as methyl or toluyl. In words relative to the above reaction diagram, a 6-hydroxyethylpenicillanate [F. DiNinno, et al., J. Org. Chem., 42, 2960 (1977)] 1 is converted to the corresponding sulfonate or sulfate ester 2 by procedures analogous to those disclosed in co-pending, commonly assigned U.S. Pat. application Ser. No. 733,655 filed Oct. 18, 1976, now abandoned, which is incorporated herein by reference. Typically, the intermediate species 2 as a sulfonate is prepared by treating 1 in a solvent such as methylene chloride, THF, dioxane, or the like with a sulfonating agent such as methane sulfonyl chloride, toluene sulfonyl chloride or the like in the presence of base such as triethylamine, pyridine, 4-dimethylaminopyridine, NaH or the like at a temperature of from −15° to 25° C for from 1 to 10 hours. Sulfate ester embodiments of intermediate species 2 ($R^2$ is $-O\ominus M\oplus$) are also suitable starting materials and have the following structural formula:

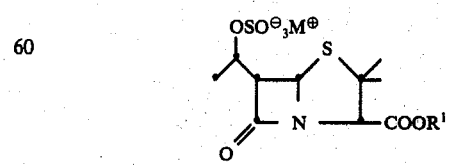

wherein M and $R^1$ are as defined above.

The enelactam intermediate 3 is prepared from 2 by treating 2 with base such as $NaHCO_3$, $HPO_4$, triethylamine, 1,4-diazabicyclo[2,2,2]octane or the like in a solvent such as benzene, THF, dioxane or the like at a temperature of from −20° to 100° C for 1 to 20 hours.

The 6-ethyl species 4 is obtained from 3 by reduction, preferably by treating 3 in a solvent such as ethanol, ethylacetate, dioxane, benzene or the like in the presence of a hydrogen catalyst such as PtO$_2$, RuO$_2$, Pt/C, or the like in the presence of 1 to 4 atmospheres of hydrogen at a temperature of from 0° to 25° C for from 0.5 to 24 hours.

The 6-ethyl sulfoxide species 5 is obtained from 4 by oxidation utilizing well established procedures known to the art. Typically, 4 is treated with an oxidizing agent such as m-chloroperbenzoic acid, peracetic acid, or the like in a solvent such as methylene chloride, chloroform, or the like at a temperature of from −78° C to 25° C for from 0.25 to 24 hours to provide 5.

The de-blocking procedure may be accomplished by any of a variety of well-known procedures such as hydrolysis or hydrogenation. Preferably the carboxyl blocking group R is removed by hydrogenation in a solvent such as a loweralkanol, for example, ethanol in the presence of a hydrogenation catalyst such as palladium, platinum or oxides thereof under 1–40 atmospheres of hydrogen at from 0° to 50° C for from 1 to 10 hours. Salts of the free acid are easily prepared by treatment of the free acid dissolved in an organic solvent such as ethyl acetate, acetone, chloroform, or the like with an equivalent amount of an inorganic base such as sodium bicarbonate, sodium hydroxide, calcium carbonate or the like, evaporating the organic solvent and lyophilizing the aqueous phase.

The products of this invention (I) form a wide variety of pharmacologically acceptable salts with inorganic and organic bases; these include, for example, metal salts derived from alkali metal or alkaline earth metal hydroxides, carbonates or bicarbonates and salts derived from primary, secondary or tertiary amines such as monoalkylamines, dialkylamines, trialkylamines, lower alkanolamines, di-loweralkanolamines, lower alkylenediamines, N,N-diaralkyl lower alkylenediamines, aralkylamines, amino substituted lower alkanols, N,N-di-lower alkylamino substituted lower alkanols, amino-, polyamino- and guanidino-substituted lower alkanoic acids and nitrogen containing heterocyclic amines. Representative examples include salts derived from sodium hydroxide, sodium carbonate, sodium bicarbonate, potassium carbonate, potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like. Salts of the primary amine of I with pharmaceutically acceptable organic and inorganic acids are also The compounds of the present invention, I, and salts thereof are valuable antimicrobial substances which are active against various gram-positive and gram-negative pathogens. Thus, the free acid and especially the salts thereof such as amine and metal salts, particularly the alkali metal and alkaline earth metal salts, are useful bactericides and can be used for removing susceptible pathogens from dental and medical equipment, for separating microorganisms, and for therapeutic use in humans and animals. For this latter purpose pharmacologically acceptable salts with inorganic and organic bases such as those known in the art and used for the administration of penicillins and cephalosporins can be utilized. For example, salts such as alkali metal and alkaline earth metal salts, and primary, secondary and tertiary amine salts can be used for this purpose. These salts can be combined with pharmaceutically acceptable liquid and solid vehicles to form suitable dosage unit forms such as pills, tablets, capsules suppositories, syrups, elixirs and the like which can be prepared in accordance with procedures well known in this art.

The novel compounds are valuable antibiotics active against various gram-positive and gram-negative bacteria and, accordingly, find utility in human and veterinary medicine. The compounds of this invention can therefore be used as antibacterial drugs for treating infections caused by gram-positive or gram-negative bacteria, for example against *Staphylococcus aureus, Escherichia coli, Klebsiella pneumoniae, Bacillus subtilis, Salmonella typhosa, Pseudomonas* and *Bacterium proteus.* The antibacterials of the invention may further be utilized as additives to animal feedingstuffs, for preserving foodstuffs and as disinfectants. For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water of paper mills to inhibit the growth of harmful bacteria.

The products of this invention may be used alone or in combination as an active ingredient in any one of a variety of pharmaceutical preparations. These antibiotics and their corresponding salts may be employed in capsule form or as tablets, powders or liquid solutions or as suspensions or elixirs. They may be administered orally, intravenously or intramuscularly.

The compositions are preferably presented in a form suitable for absorption by the gastro-intestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers for example, lactose, sugar, maizestarch, calcium phosphate, sorbitol or glycine; lubricants, for example, magnesium stearate, talc, polyethylene glycol, silic; disintegrants, for example, potato starch or acceptable wetting agents such as sodium lauryl sulphate. The tablets may be coated according to methods well known in the art. Oral liquid preparations may be in the form or aqueous or oily suspension, solution, emulsions, syrups elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible oils, for example almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g., cocoa butter or other glyceride.

Compositions for injection may be presented in unit dose form in ampules, or in multidose containers with an added preservative. The compositions may take such forms as suspensions, solutions, or emulsions in oil or aqueous vehicles, and may contain formulatory agents such as suspending, stabilizing and/or dispersing agents. Alternatively, the active ingredient may be in powder form for reconstitution with a suitable vehicle, e.g., sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical applications may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like. In addition, there may also be included in the composition other active ingredients to provide a broader spectrum of antibiotic activity.

For veterinary medicine the composition may, for example, be formulated as an intromammary preparation in either long acting or quick-release bases.

The dosage to be administered depends to a large extent upon the condition of the subject being treated and the weight of the host, the route and frequency of administration, the parenteral route being preferred for generalized infections and the oral route for intestinal infections. In general, a daily oral dosage consists of from about 15 to about 600 mg. of active ingredient per kg. of body weight of the subject in one or more applications per day. A preferred daily dosage for adult humans lies in the range of from about 80 to 120 mg of active ingredient per kg. of body weight.

The instant compositions may be administered in several unit dosage forms as, for example, in solid or liquid orally ingestible dosage form. The compositions per unit dosage, whether liquid or solid may contain from 0.1% to 99% of active material, the preferred range being from about 10–60%. The composition will generally contain from 15 mg. of about 1500 mg. of the active ingredient; however, in general, it is preferable to employ a dosage amount in the range of from about 250 mg to 1000 mg. In parenteral administration the unit dosage is usually the pure compound in a slightly acidified sterile water solution or in the form of a soluble powder intended for solution.

The following examples illustrate but do not limit the product, process, compositional or method of treatment aspects of the present invention. All temperatures are in ° C.

EXAMPLE 1

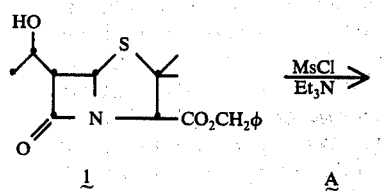

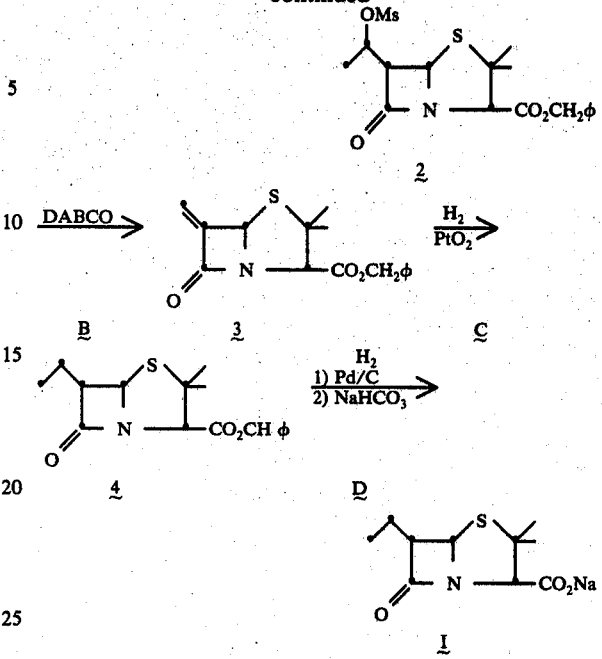

Step A

Preparation of 2

To a stirred solution of 614 mg (1.8 mmol) of benzyl-6-[1-hydroxyethyl]penicillantes (1) and 296 mg (2.9 mmol) triethylamine in 10 ml of dry methylene chloride at 0° C under an atmosphere of nitrogen is added dropwise via syringe 184 μl (2.4 mmol) of neat mesylchloride. The mixture is stirred at 0° C for 45 minutes and is partitioned between $CH_2Cl_2$ and ice-$H_2O$. The organic phase is separated, dried ($MgSO_4$), filtered, and evaporated to afford 743 mg (100%) of pure mesylates 2: NMR ($CDCl_3$)δ : 1.35 (s, 3H), 1.4 (d, J=6Hz, 3H), 1.6 (s, 3H), 3.03 (s, 3H), 3.7 (dd, J=5, 11Hz, 1H), 4.43 (s, 1H), 5.1 (m, 1H), 5.1 (s, 2H), 5.35 (d, J=5 Hz, 1H), and 7.27 (s, 5H).

Step B

Preparation of Enelactams 3

A stirred mixture of 743 mg (1.8 mmol) of 2 from Step A and 242 mg (2.16 mmol) 1,4-diazabicyclo[2,2,2]octane (DABCO) in 10 ml of benzene is refluxed at 90° under a nitrogen atmosphere for 1.6 hours. The cooled mixture is partitioned between EtOAc and $H_2O$ and the organic phase is separated, washed with aqueous brine, dried ($MgSO_4$), filtered and evaporated. Purification by chromatography on silica gel yields 441 mg (77%) of enelactams 3: IR ($CHCl_3$) 1754 and 1709 cm$^{-1}$; NMR ($CDCl_3$)δ : 1.37 (s, 3H), 1.53 (S, 3H), 1.76 and 2.02 (d's, J=7Hz, 3H), 4.47 (s, 1H), 5.13 (s, 2H), 5.57 and 5.67 (bs's, 1H), 5.83 (app. q, J=7Hz) and 6.23 (octet, J=1 and 7Hz, 1H), 7.27 (s, 5H); m/e 317 (M$^+$), 289, 250, 243, 226, 215, 199, 190, 182, 91.

Step C

Preparation of Benzyl-6-ethylpenicillante (4)

A mixture of 441 mg (1.4 mmol) of enelactams 3 from Step B and 100 mg $PtO_2$ in 10 ml of EtOAc is hydrogenated at 25° C and atmospheric pressure for 22 hours and at 50 psi for 5 hours. The catalyst is removed by filtration and washed well with EtOAc. The filtrate is evaporated and the residue so obtained is purified by plate layer chromatography [one development methylene chloride] to provide 399.2 mg (90%) of 4: IR (CHCl$_3$); 1750 cm$^{-1}$; NMR (CDCl$_3$) δ : 0.91 (t, J=7Ha, 3H), 1.35 (s, 3H), 1.53 (s, 3H), 2.79 (m, 2H), 3.43 (ddd, J=4.5, 7.0, 10.0 Hz, 1H), 4.37 (s, 1H), 5.13 (s, 2H), 5.4 (d, J=4.5 Hz, 1H), 7.31 (s, 5H); m/e 319 (M$^+$), 291, 250, 91.

Step D

Preparation of Sodium 6-ethylpenicillanate (I)

A mixture of 100 mg (0.3 mmol) of 4 from Step C above and 150 mg of 10% Pd/C in 10 ml methanol, 2 ml H$_2$O, and 1 ml 0.1N pH 7 phosphate buffer is hydrogenated at 25° C and atmospheric pressure for 25 minutes. The catalyst is removed by filtration through solka-floc and washed well with methanol. The filtrate is concentrated under reduced pressure and diluted with water. The aqueous mixture is taken to pH 9.0 with dilute aqueous sodium bicarbonate and is then extracted throughly with ethylacetate. The aqueous phase is separated and acidified to pH 2.5 with aqueous 2.5N hydrochloric acid. The acidified mixture is extracted thoroughly with ethylacetate and the combined extracts are dried (MgSO$_4$), filtered and evaporated to yield free acid I.

The free acid I 70 mg (0.3 mmol) is dissolved in 5 ml of acetone and is treated with 2 ml of an aqueous solution of NaHCO$_3$ (25.7 mg, 0.3 mmol). The acetone is removed under reduced pressure and the remaining aqueous solution is lyopholized to yield the title compound.

EXAMPLE 2

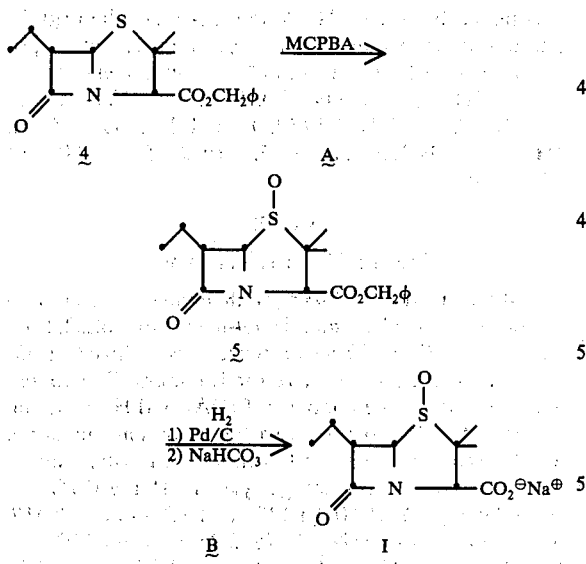

Step A

Preparation of 5

To a stirred solution of 179.8 mg (0.56 mmol) of benzyl-6-ethylpenicillanate in 2 ml of dry methylene chloride at 25° C is added 97.3 mg (0.56 mmol) of m-chloroperbenzoic acid. The mixture is stirred at 25° C under a nitrogen atmosphere for 48 minutes. The mixture is partitioned between ethylacetate and aqueous sodium bicarbonate. The organic phase is separated, washed with saturated sodium chloride, dried, (MgSO$_4$), filtered, and evaporated. The residue is purified by preparative layer chromatography [two developments φH-EtOAc (4:1)] to provide 131.0 mg (70%) of major sulfoxide 5, as a white solid, m.p. 77°–79° C (isopropanol-hexane) : NMR (CDCl$_3$) δ : 1.13 (t, J=7Hz, 3H), 1.23 (s, 3H), 1.53 (s, 3H), 1.83 (m, 2H), 3.67 (m, 1H), 4.37 (s, 1H), 4.62 (d, J=4.5 Hz, 1H), 5.2 (s, 2H), 7.37 (s, 5H).

Step B

Preparation of I

A mixture of 100 mg (0.3 mmol) of 5 from Step A above and 165 mg of 10% Pd/C in 10 ml methanol, 2 ml H$_2$O, and 1 ml 0.1N pH 7 phosphate buffer is hydrogenated at 25° C and atmospheric pressure for 25 minutes. The catalyst is removed by filtration through solka-floc and washed well with methanol. The filtrate is concentrated under reduced pressure and diluted with water. The aqueous mixture is taken to pH 9.0 with aqueous sodium bicarbonate solution and is extracted thoroughly with ethylacetate. The aqueous phase is separated and carefully acidified in the cold with 2.5N HCl to pH 2.5. The cold aqueous solution is thoroughly extracted with ethylacetate and the combined extracts are dried (Na$_2$SO$_2$), filtered and evaporated to afford the pure sulfoxide penicillanic acid I.

The free acid (50 mg, 0.2 mmol) is dissolved in 5 ml of acetone and is treated with 16.8 mg (0.2 mmol) of sodium bicarbonate dissolved in 2 ml of H$_2$O at 25° C. The acetone is removed under reduced pressure and the aqueous phase is lyophilized to produce the corresponding sodium salt I.

EXAMPLE 3

Preparation of Pharmaceutical Compositions

One such unit dosage form consists in mixing 120 mg. 6-ethylpenicillanic acid with 20 mg. of lactose and 5 mg of magnesium stearate and placing the 145 mg. mixture into a No. 3 gelatin capsule. Similarly, by employing more of the active ingredient and less lactose, other dosage forms can be put in No. 3 gelatin capsules and should it be necessary to mix more than 145 mg of ingredients together, larger capsules such as compressed tablets and pills can also be prepared. The following examples are illustrative of the preparation of pharmaceutical formulations:

| TABLET | PER TABLET |
| --- | --- |
| 6-ethylpenicillanic acid | 125 mg |
| Cornstarch, U.S.P. | 6 mg |
| Dicalcium Phosphate | 192 mg |
| Lactose, U.S.P. | 190 mg |

The active ingredient is blended with the dicalcium phosphate, lactose and about half of the cornstarch. The mixture is then granulated with 15% cornstarch paste (6 mg) and rough-screened. It is dried at 45° C and screened again through No. 16 screens. The remaining cornstarch and magnesium stearate, being the balance, is added and the mixture is compressed into tablets, approximately 0.5 inch in diameter each weighing 800 mg.

PARENTERAL SOLUTION

Ampoule

6-Ethylpenicillanic acid — 500 mg
diluent: sterile water for injection — 2 ml

OPTHALMIC SOLUTION

Ampoule

6-Ethylpenicillanic acid — 100 mg
Hydroxypropylmethyl cellulose — 5 mg
Sterile Water — 1 ml

OPTIC SOLUTION

Ampoule

6-Ethylpenicillanic acid — 100 mg
Benzalkonium Chloride — 0.1 mg
Sterile Water — 1 ml

TOPICAL OINTMENT

6-Ethylpenicillanic acid — 100 mg
Polyethylene Glycol 4000 U.S.P. — 400 mg
Polyethylene Glycol 400 U.S.P. — 1.0 gram The active ingredient in the above formulations may be administered alone or in combination with other biologically active ingredients as, for example, with other antibacterial agents such as lincomycin, a penicillin, streptomycin, novobiocin, gentamicin, neomycin, colistin and kanamycin, or with other therapeutic agents such as probenecid.

What is claimed is:

1. A compound having the structure:

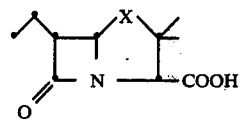

wherein: X is S or SO; and the pharmaceutically acceptable salts thereof.

2. A compound having the structure:

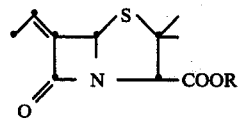

wherein R is a readily removable protecting group.

3. A pharmaceutical composition comprising, in unitary dosage form, a therapeutically effective amount of a compound according to claim 1 and a pharmaceutical carrier therefor.

* * * * *